United States Patent [19]

Urdea

[11] Patent Number: 5,380,833

[45] Date of Patent: Jan. 10, 1995

[54] POLYNUCLEOTIDE REAGENTS CONTAINING SELECTABLE CLEAVAGE SITES

[75] Inventor: Michael S. Urdea, Alamo, Calif.

[73] Assignee: Chiron Corporation, Emeryville, Calif.

[21] Appl. No.: 806,642

[22] Filed: Dec. 13, 1991

Related U.S. Application Data

[60] Division of Ser. No. 251,152, Sep. 29, 1988, Pat. No. 5,118,605, which is a continuation-in-part of Ser. No. 661,508, Oct. 16, 1984, Pat. No. 4,775,619.

[51] Int. Cl.[6] ......................... C07H 21/04; C12Q 1/68
[52] U.S. Cl. ........................................ 536/22.1; 435/6; 436/501; 536/23.1; 536/24.1; 536/24.3; 536/24.2; 536/24.31; 536/24.32; 536/24.33; 536/25.3; 536/25.4; 935/78; 935/88
[58] Field of Search ............... 435/6, 810, 91, 91.1, 435/91.2; 436/501; 536/25-27, 22.1, 25.3, 23.1, 25.4, 24.1, 24.2, 24.3-24.33; 935/7, 9, 88, 78

[56] References Cited

PUBLICATIONS

Maniatis et al. (1982) *Molecular Cloning, A Laboratory Manual* (Cold Spring Harbor Lab., CSH, New York) pp. 214–223.

Arndt–Jovin et al. (1975) Eur. J. Biochem., vol. 54, pp. 411–418.

Ashley et al. (1984) Anal. Bioch., vol. 140, pp. 95–103.

*Primary Examiner*—Margaret Parr
*Assistant Examiner*—Ardin H. Marschel
*Attorney, Agent, or Firm*—Dianne E. Reed; Kenneth M. Goldman; Robert P. Blackburn

[57] ABSTRACT

Novel methods for assaying a nucleic acid analyte are provided, which employ polynucleotides having oligonucleotide sequences substantially homologous to a sequence of interest in the analyte, where the presence or absence of hybridization at a predetermined stringency provides for the release of a label from a support. Particularly, various techniques are employed for binding a label to a support, whereupon cleavage of either a single or double strand, a label may be released from a support, where the release of the label can be detected as indicative of the presence of a particular oligonucleotide sequence in a sample. The method finds use in diagnosis of disease, genetic monitoring, and analysis of nucleic acid mixtures.

17 Claims, 3 Drawing Sheets

(LABEL RELEASE)

FIG. 3B

POLYNUCLEOTIDE REAGENTS CONTAINING SELECTABLE CLEAVAGE SITES

This application is a divisional of U.S. patent application Ser. No. 07/251,152, filed Sep. 29, 1988 and issued Jun. 2, 1992 as U.S. Pat. No. 5,118,605, which was a continuation-in-part of U.S. patent application Ser. No. 06/661,508, filed Oct. 16, 1984 and issued Oct. 4, 1988 as U.S. Pat. No. 4,775,619.

BACKGROUND OF THE INVENTION

1. Field of the Invention

The ability to synthesize oligonucleotide sequences at will and to clone polynucleotide sequences prepared by synthetic procedures or obtained from naturally occurring sources has greatly expanded the opportunities for detecting the presence of specific sequences in an extended oligonucleotide sequence, e.g., chromosome(s), mixture of sequences, mRNAs, or the like. Interest in specific sequences may involve the diagnosis of the presence of pathogens, the determination of the presence of alleles, the presence of lesions in a host genome, the detection of a particular mRNA or the monitoring of a modification of a cellular host, to mention only a few illustrative opportunities. While the use of antibodies to perform assays diagnostic of the presence of various antigens in samples has seen an explosive expansion in techniques and protocols since the advent of radioimmunoassay, there has been until recently no parallel activity in the area of the DNA probes. Therefore, for the most part, detection of sequences has involved various hybridization techniques requiring the binding of a polynucleotide sequence to a support and employing a radiolabeled probe.

In view of the increasing capability to produce oligonucleotide sequences in large amounts in an economical way, the attention of investigators will be directed to providing for simple, accurate and efficient techniques for detecting specific oligonucleotides sequences. Desirably, these techniques will be rapid, minimize the opportunity for technician error, be capable of automation, and allow for simple and accurate methods detection. Toward this end, there have already been efforts to provide for means to label oligonucleotide probes with labels other than radioisotopes and for improving the accuracy of transfer of DNA sequences to a support from a gel, as well as improved methods for derivatizing oligonucleotides to allow for binding to a label. There continues to be a need for providing new protocols which allow for flexibility in detecting DNA sequences of interest in a variety of situations where the DNA may come from diverse sources.

2. Description of the Prior Art

Meinkoth and Wahl, *Anal. Biochemistry* (1984) 138:267–284, provide an excellent review of hybridization techniques. Leary, et al., *Proc. Natl. Acad. Sci. USA* (1983) 80:4045–4049, describe the use of biotinylated DNA in conjunction with an avidin-enzyme conjugate for detection of specific oligonucleotide sequences. Ranki et al., *Gene* (1983) 21:77–85 describe what they refer to as a "sandwich" hybridization for detection of oligonucleotide sequences. Pfeuffer and Helmrich, *J. of Biol. Chem.* (1975) 250:867–876 describe the coupling of guanosine-5' -0-(3-thiotriphosphate) to Sepharose 4B. Bauman, et al., *J. of Histochem. and Cytochem.* (1981) 20:227–237, describe the 3'-labeling of RNA with fluorescers. PCT Application W0/8302277 describes the addition to DNA fragments of modified ribonucleotides for labeling and methods for analyzing such DNA fragments. Renz and Kurz, *Nucl. Acids Res.* (1984) 12:3435–3444, describe the covalent linking of enzymes to oligonucleotides. Wallace, DNA Recombinant Technology (Woo, S., Ed.) CRC Press, Boca Raton, Fla., provides a general background of the use of probes in diagnosis. Chou and Merigan, *N. Eng. J. of Med.* (1983) 308:921–925, describe the use of a radioisotope labeled probe for the detection of CMV. Inman, Methods in Enzymol. 34B, 24 (1974) 30–59, describes procedures for linking to polyacrylamides, while Parikh, et al., Methods in Enzymol. 34B, 24 (1974) 77–102, describe coupling reactions with agarose. Alwine, et al., *Proc. Natl. Acad. Sci. USA* (1977) 74:5350–5354, describe a method of transferring oligonucleotides from gels to a solid support for hybridization. Chu, et al., *Nucl. Acids Res.* (1983) 11:6513–6529, describe a technique for derivatizing terminal nucleotides. Ho, et al., *Biochemistry* (1981) 20:64–67, describe derivatizing terminal nucleotides through phosphate to form esters. Ashley and MacDonald, *Anal. Biochem.* (1984) 140:95–103, report a method for preparing probes from a surface bound template. These references which describe techniques are incorporated herein by reference in support of the preparation of labeled oligonucleotides.

SUMMARY OF THE INVENTION

Methods are provided for the detection of specific nucleotide sequences employing a solid support, at least one label, and hybridization involving a sample and a labeled probe, where the presence or absence of duplex formation results in the ability to modify the spatial relationship between the support and label(s). Exemplary of the technique is to provide a cleavage site between the label and support through duplexing of a labeled probe and sample DNA, where the duplex is bound to a support. The cleavage site may then be cleaved resulting in separation of the support and the label(s). Detection of the presence or absence of the label may then proceed in accordance with conventional techniques.

A primary advantage of the invention over the art is that the present method enables one to distinguish between specific and nonspecific binding of the label. That is, in the prior art, label is typically detected on a solid support, i.e., the sample is affixed to the support and contacted with a complementary, labeled probe; duplex formation is then assayed on the support. The problem with this method is that label can and does bind to the support in the absence of analyte. This direct binding of the label to the support is referred to herein as "nonspecific" binding. If any significant amount of nonspecific binding occurs, label will be detected on the support regardless of the presence of analyte, giving false positive results.

By contrast, in the present method, label is detected only when the analyte of interest is present, i.e., only "specific" binding is detected. In a preferred embodiment, this is done by introducing a cleavage site between a support and the selected label, through a duplex between the sample and one or more probes. The cleavage site may be a restriction endonuclease cleavable site, as described in the related, commonly assigned U.S. patent application Ser. No. 06/661,508, now U.S. Pat. No. 4,775,619, or it may be one of a number of types of chemically cleavable sites, e.g., a disulfide linkage, periodate-cleavable 1,2-diols, or the like. In an alternative embodiment, specifically bound label is released by a strand replacement procedure, wherein after binding of the label to the support through an analyte/probe complex, a DNA strand is introduced that is complementary to a segment of the analyte/probe complex and is selected so as to replace and release the labeled portion thereof.

DESCRIPTION OF THE SPECIFIC EMBODIMENTS

Detection of specific sequences is achieved using hybridization, whereby duplexing of the sample DNA and a probe affects the ability to modify the spatial relationship between a label and a support. In this manner, the presence or absence of a particular sequence in a sample can be readily determined by the amount of label which is freed into the medium.

The subject method allows for varying protocols and reagents where the sample nucleic acid may be bound to a support or free in solution. In a preferred embodiment, the method involves forming a nucleic acid duplex where a label is separated from a support by a selectively cleavable bond, so that the amount of label released under conditions providing selective cleavage is a measure of the presence and amount of a sequence of interest in a nucleic acid sample. The selectable cleavage site may be as a result of formation of a restriction enzyme recognition site through homoduplexing, or the presence of such selectable cleavage site in the single-stranded polynucleotide chain may be a result of the prior introduction of such site into the single-stranded chain.

A reagent will be employed which will include a polynucleotide sequence having an oligonucleotide sequence of interest that hybridizes to the nucleic acid analyte. This reagent will sometimes be referred to herein as a "capture probe", which in the present method, is bound to the selected solid support. A labeling probe will also be employed, which may or may not include the sequence of interest.

In the first, preferred embodiment, the subject method involves the forming of a polynucleotide duplex in a hybridization medium resulting in a label bound to a support through a selectable cleavage site. Various protocols may be employed where the sample DNA is bound to a support or dispersed in a solution.

In order to distinguish the various nucleotide sequences involved, the following terms will be used:

nucleic acid sample—sample suspected of containing a nucleic acid sequence having an oligonucleotide sequence of interest;

nucleic acid analyte—DNA or RNA in said nucleic said sample having an oligonucleotide sequence of interest;

oligonucleotide sequence of interest—a DNA or RNA sequence which may be all or part of a nucleotide chain, usually at least six bases, more usually at least about 10 bases, preferably at least about 16 bases, which may be 5 kb or more, usually not more than 0.2 kb, which is diagnostic of a property to be detected, where the property may be a gene or sequence diagnostic of a hereditary trait, pathogen, etc.;

polynucleotide sequence—DNA or RNA sequences employed as reagents for detection of the oligonucleotide sequence of interest, which polynucleotide sequence may be Labeled or unlabeled, bound or unbound to a support, and may or may not include a sequence complementary to the oligonucleotide sequence of interest. There will be one to two polynucleotide sequences, which individually or in conjunction with the nucleic acid analyte will act as a bridge between a label and a support, with a selectably cleavable site intermediate the label and support; and selectably cleavable site—a functionality or plurality of functionalities which can be selectively cleaved and may include restriction sites, phosphate esters, purines, peptide bonds, etc.

For convenience of description, the preferred embodiment of the subject invention wherein a selectable cleavage site is created will be divided into four primary sub-embodiments. In the first of these (see FIG. 2A) the reagent employed is a single component, which is a polynucleotide joined proximal to one end to a support and joined proximal to the opposite end to one or more detectable labels. The polynucleotide will include a region of at least four successive nucleotides homoduplexing with a sequence of interest, where such sequence includes a restriction site, which is intermediate the support and label.

In the second case (See FIG. 2B), the reagent employed will have two components which will vary with whether the nucleic acid sample is bound or unbound to a support and the nature of the selectable cleavage site. Where the nucleic acid sample is bound to the support, the two components will be (1) a bridging polynucleotide sequence and (2) a polynucleotide sequence complementary and hybridizing to a portion of the bridging polynucleotide sequence. Either the bridging or complementary polynucleotide sequence may be labeled. The presence of the label bound to the bridging sequence will be limited to when the duplex of the bridging and analyte polynucleotide sequences define a restriction site as the selectable cleavage site. Otherwise, only the complementary sequence will be labeled. Besides having a sequence duplexing with the complementary sequence, the bridging polynucleotide sequence will have a region duplexing with the oligonucleotide sequence of interest.

Where the sample nucleic acid is in solution, the two components will be (1) a first polynucleotide sequence bound to a support, which has a region complementary to a sequence present in the nucleic acid analyte, which sequence may or may not define a restriction site and may or may not define the oligonucleotide sequence of interest; and (2) a labeled second polynucleotide sequence which as a region complementary to a sequence present in the nucleic acid analyte, which region is subject to the same limitations as the region of the first polynucleotide sequence. At least one of the duplexed regions will define a sequence of interest. In the absence of one of the regions defining a restriction site or in addition to the presence of a restriction site, there will be a selectable cleavage site present with the first or second polynucleotide sequence.

In a third case (see FIG. 2C), the analyte is bound to a support and the reagent employed is a single component which is a labeled polynucleotide sequence having a region complementary to the oligonucleotide sequence of interest which may define a restriction site. The restriction site and/or a functionality present on the labeled polynucleotide sequence may serve as a selectable cleavage site.

In a fourth case (see FIG. 2D), a capture probe is provided which is a polynucleotide chain bound to a solid support via a linkage "Y", and at its opposing end is complementary to a first sequence present in the nucleic acid analyte. A labeling probe comprising a Labeled second polynucleotide chain has a region complementary to a second sequence in the analyte that is distinct from and does not overlap with the first sequence. The linkage designated "Y" in FIG. 2D represents any conventional means of binding a probe to a support. The linkage "X" is a selectable cleavage site, i.e., a chemically clearable linkage such as a disulfide bond, periodate-clearable 1,2-diols, or the like.

The nucleic acid containing sample will be combined with the appropriate reagent under conditions where duplex formation occurs between complementary sequences. The mixture is allowed to hybridize under conditions of predetermined stringency to allow for at Least heteroduplex formation or homoduplex formation over an oligonucleotide sequence of interest. After a sufficient time for hybridization to occur, the support may be separate from the supernatant and washed free of at least substantially all of the non-specifically bound label. The oligonucleotides bound to the support are then treated with one or more reagents, which results in cleavage of at least one strand and release of label bound to support.

Depending upon the presence of a particular sequence in the sample resulting in duplex formation, release of the label(s) bound to the support will be observed. Various protocols may be employed, where normally the supernatant medium may be assayed for the presence of the label, although in some instances the support may be measured. Protocols and reagents may be employed, where a physical separation of the support from the supernatant may or may not be required.

The subject method can be used for the detection of oligonucleotide sequences, either DNA or RNA, in a wide variety of situations. One important area of interest is the detection of pathogens, viruses, bacteria, fungi, protozoa, or the like, which can infect a particular host. See for example, U.S. Pat. No. 4,358,535. Another area of interest is the detection of alleles, mutations or lesions present in the genome of a host, such as involved in amniocentesis, genetic counseling, host sensitivity or susceptibility determinations, and monitoring of cell populations. A third area of interest is the determination of the presence of RNA for such diverse reasons as monitoring transcription, detecting RNA viruses, differentiating organisms through unexpressed RNA, and the like. Other areas of interest, which are intended to be illustrative, but not totally inclusive, include monitoring modified organisms for the presence of extrachromosomal DNA or integrated DNA, amplifications of DNA sequences, the maintenance of such sequences.

The physiological samples may be obtained from a wide variety of sources as is evident from the varied purposes for which the subject method may be used. Sources may include various physiological fluids, such as excreta, e.g., stool, sputum, urine, saliva, etc.; plasma, blood, serum, ocular lens fluids, spinal fluid, lymph, and the like. The sample may be used without modification or may be modified by expanding the sample, cloning, or the like, to provide an isolate, so that there is an overall enhancement of the DNA or RNA and reduction of extraneous RNA or DNA. Viruses may be plated on a lawn of compatible cells, so as to enhance the amount of viral DNA; clinical isolates may be obtained by the sample being streaked or spotted on a nutrient agar medium and individual colonies assayed; or the entire sample introduced into a liquid broth and the cells selectively or non-selectively expanded. The particular manner in which the sample is treated will be dependent upon the nature of the sample, the nature of the DNA or RNA source, the amount of oligonucleotide sequence of interest which is anticipated as being present as compared to the total amount of nucleic acid present, as well as the sensitivity of the protocol and label being employed.

Either the sample nucleic acid or the reagent polynucleotide may be bound, either covalently or non-covalently, but in any event non-diffusively, to the support. (In the case of the embodiment represented by FIG. 2D, the capture probe alone is bound to the solid support.) Where a sample nucleic acid is bound to the support, various supports have found particular use and to the extent, those supports will be preferred. These supports include nitrocellulose filters, diazotized paper, ecteola paper, or other support which provides such desired properties as low or no non-specific binding, retention of the nucleic acid sample, ease of manipulation, and allowing for various treatments, such as growth or organisms, washing, heating, transfer, and label detection, as appropriate.

To the extent that a component of the polynucleotide reagent is bound to the support, the type of support may be greatly varied over the type of support involved with the sample oligonucleotide. The support may include particles, paper, plastic sheets, container holder walls, dividers, millipore filters, etc., where the materials may include organic polymers, both naturally occurring and synthetic, such as polysaccharides, polystyrene, polyacrylic acid and derivatives thereof, e.g., polyacrylamide, glass, ceramic, metal, carbon, polyvinyl chloride, protein, and the like. The various materials may be functionalized or non-functionalized, depending upon whether covalent or non-covalent bonding is desired.

Where the sample nucleic acid is bound to the support, depending upon the particular support, heating may be sufficient for satisfactory binding of the nucleic acid. In other situations, diazo groups may be employed for linking to the nucleic acid. Where, however, the polynucleotide reagent component is bound to the support, a wide variety of different techniques may be employed for ensuring the maintenance of the polynucleotide reagent bound to the support. For example, supports can be functionalized, to have active amino groups for binding, resulting from the binding of alkylamines, hydrazides, or thiosemicarbazides to the support. One can then add, by means of a terminal transferase, a ribonucleotide to a DNA polynucleotide reagent. Upon glycol cleavage with an appropriate oxidant, e.g., periodate, osmium tetroxide plus hydrogen peroxide, lead tetraacetate, or the like, a dialdehyde is formed, which will then bind to the amino group on the surface to provide a monosubstituted amino or disubstituted amino group. Alternatively, one can provide for a maleimide group which with thiophosphate will form the alkylthioester. Various techniques described by Parikh, et al., supra and by Inman, supra for agarose and polyacrylamide may be employed, which techniques may have application with other materials.

The total number of polynucleotide reagent components on the support available in the assay medium will vary, for the most part being determined empirically. Desirably, a relatively high concentration per unit surface area of polynucleotide to available functional groups on the support should be employed, so long as the polynucleotide density does not interfere with hybridization.

The size of the polynucleotide will vary widely, usually being not less than about 15 bases and may be 50 bases or more, usually not exceeding about 500 bases, more usually not exceeding 250 bases. There will usually be a region in the polynucleotide reagent component homologous with a sequence in the nucleic acid sample, usually the sequence of interest, of at least six bases, usually at least 12 bases. The region for hybridization may be 16 bases or more, usually not exceeding about 1 kbp, where perfect homology is not required, it being sufficient that there be homology to at least about 50%, more preferably homology to at least 80%. (By percent homology is intended complementary, ignoring non-complementary insertions which may loop out, insertions being greater than five bases.)

Particularly, where one is interested in a group of allelic genes, a number of different strains, or related species, where the messenger RNA or genomic portion is highly conserved but nevertheless is subject to polymorphisms, it will frequently be desirable to prepare a probe which reflects the differences and optimizes the homology for all the sequences of interest, as against any particular sequence.

The label of the labeled polynucleotide reagent component may be joined to the polynucleotide sequence through the selectively cleavable site or through a link which is retained during the assay. A wide variety of labels may be employed, where the label may provide for a detectable signal or means for obtaining a detectable signal.

Labels therefore include such diverse substituents as ligands, radioisotopes, enzymes, fluorescers, chemiluminescers, enzyme suicide inhibitors, enzyme cofactors, enzyme substrates, or other substituent which can provide, either directly or indirectly, a detectable signal.

Where ligands are involved, there will normally be employed a receptor which specifically binds to the ligand, e.g., biotin and avidin, 2,4'-dinitrobenzene and anti(2,4-dinitrobenzene)IgG, etc., where the receptor will be substituted with appropriate labels, as described above. In this manner, one can augment the number of labels providing for a detectable signal per polynucleotide sequence.

For the most part, the labels employed for use in immunoassays can be employed in the subject assays. These labels are illustrated in U.S. Pat. Nos. 3,850,752 (enzyme); 3,853,914 (spin label); 4,160,016 (fluorescer); 4,174,384 (fluorescer and quencher); 4,160,645 (catalyst); 4,277,437 (chemiluminescer); 4,318,707 (quenching particle); and 4,318,890 (enzyme substrate).

Illustrative fluorescent and chemiluminescent labels include fluorescein, rhodamine, dansyl, umbelliferone, biliproteins, luminol, etc.

Illustrative enzymes of interest include horse radish peroxidase, glucose-6-phosphate dehydrogenase, acetylcholinesterase, $\beta$-galactosidase, $\chi$-amylase, uricase, malate dehydrogenase, etc. That is, the enzymes of interest will primarily be hydrolases and oxidoreductases.

The manner in which the label becomes bound to the polynucleotide sequence will vary widely, depending upon the nature of the label. As already indicated, a ribonucleotide may be added to the oligonucleotide sequence, cleaved, and the resulting dialdehyde conjugated to an amino or hydrazine group. The permanence of the binding may be further enhanced by employing reducing conditions, which results in the formation of an alkyl amine. Alternatively, the label may be substituted with an active halogen, such as alpha-bromo or -chloroacetyl. This may be linked to a thiophosphate group or thiopurine to form a thioether. Alternatively, the label may have maleimide functionality, where a mercapto group present on the polynucleotide will form a thioether. The terminal phosphate of the polynucleotide may be activated with carbodiimide, where the resulting phosphorimidazolide will react with amino groups or alcohols to result in phosphoramidates or phosphate esters. Polypeptide bonds may be formed to amino modified purines. Thus, one has a wide latitude in the choice of label, the manner of linking, and the choice of linking group.

By combining the polynucleotide reagent with the sample, any nucleic acid analyte present will become bound to the support. The amount of label released from the support upon cleavage of the selectable cleavage site will be related to the presence of analyte, where the amount of analyte may also be determined quantitatively.

The modification of the spatial relationship between the label and the support can be achieved in a number of ways. As indicated, there can be at least one recognition site common to the probe and the same polynucleotide, which can be digested with a restriction enzyme, thus releasing the probe from the support. A wide variety of restriction enzymes are available which can detect four base, six base, or eight base recognition sites, where cleavage can be blunt-ended or staggered, may occur at the recognition site or distant from the recognition site. In this manner, the duplex formation of the recognition site(s) provides for the opportunity to cleave the double strand with release of the label.

The nature of the selective cleavage site may or may not depend upon the linking group. Where a restriction site is involved, the bonds involved with the reagent components need only be stable under the assay conditions. Where a restriction site is not involved, then the site will involve a bond(s) which allows for separation of the label from the support.

A phosphodiesterase may be employed where random hydrolysis will separate the label from the support. The polynucleotide may be tailed with modified nucleotides which are or may be subsequently labeled.

A wide variety of linking groups can be employed, where the nucleotides may be modified or unmodified for linkage of the label. W083/02277 reports the use of 8-aminoalkyladenosine, where a label can be bound to the amino group. The DNA polynucleotide reagent may then be tailed with the ribonucleotides so that a plurality of labels will be present at the terminus of each labeled polynucleotide. The tailed ribonucleotides may be selectively cleaved employing an RNase. This will be particularly advantageous when employing labels which interact to modify the signal. For example, fluorescers in close proximity tend to self-quench. The observed fluorescent signal can be greatly enhanced by hydrolyzing the phosphate bonds, so that the individual fluorescer molecules are randomly present in the solution. Of course, fluorescers need not be the only labels demonstrating this phenomenon, but other of the labels may also display similar effects. Where enzyme substrates or cofactors are employed, their presence on a polymer bound to a support will result in substantial steric interference with enzyme approach. Thus the depolymerization of the label and release from the support will substantially enhance the enzyme rate.

Another technique is to add a ribonucleotide to a DNA polynucleotide reagent and then cleave the ribosyl moiety to produce a dialdehyde. (See, for example, Lee, et al., Biochemistry (1970) 9:113-118.) The dialdehyde may be linked to an amino group joined to a label through a selectively cleavable site. For example, a disulfide link may be present between the Schiff's base and the label which can be cleaved by reduction, with Ellman's reagent, or the like, to release the label. Where a restriction endonuclease will be used to release of the label, then the dialdehyde can be combined with the amino functionality under reductive amination conditions. various amino sources, such as proteins, e.g., enzymes, phycobiliprotein fluorescers, receptors, such as immunoglobulins or avidin, or non-proteinaceous labels may be employed.

Another linking method involves activating a terminal phosphate with carbodiimide to form a phosphorimidazolide. (Chu, et al., Nucleic Acids Res. (1983) 11:6513-6628.) The phosphorimidazolide may be reacted with amines to form phosphoramidates. As before, the amino linking group will include the selectable cleavage site, as appropriate, which could be a pyrophosphate diester, cleavable by a pyrophosphatase, a short polypeptide which could be cleaved by a peptidase, a light-sensitive functionality such as azo, peroxy, or the like.

Another method for attaching the label involves chemical synthesis of polynucleotides with a modifiable nucleoside derivative such as a cytosine or uracil containing a 12-atom amine linker arm, followed by incorporation of a reporter group such as fluorescein or dinitrobenzene (Ruth, DNA (1984) 3:123).

Ligand substituted nucleotides can be employed where the ligand does not give a detectable signal directly, but bonds to a receptor to which is conjugated one or more labels. Illustrative examples include biotinylated nucleotides which will bind to avidin, haptens which will bind to immunoglobulins, and various naturally occurring compounds which bind to proteinaceous receptors, such as sugars with lectins, hormones and growth factors with cell surface membrane proteins, and the like.

In the embodiment represented by FIG. 2D, the selectable cleavage site may be introduced in one of two ways.

First, a crosslinking compound may be incorporated into the capture probe 1 itself, i.e., at position "X" as indicated in the figure. Any number of crosslinking agents may be used for this purpose, the only limitation being that the cleavage site introduced into the capture probe must be cleavable with reagents that are compatible with the various probes, labels, etc., used in the remainder of the method. Examples of suitable amide bond into the probe; ethylene glycolbis crosslinkers include the following:

N-hydroxy succinimide (NHS), which introduces an amide bond into the probe; ethylene glycolbis (succinimidylsuccinate) (EGS), which creates a hydroxylamine-sensitive linkage; bis[2-succinimidooxycarbonyloxy)ethyl]sulfone (BSOCOES), which gives a base-sensitive sulfone linkage; disuccinimidyl tartarate (DST), which introduces 1,2-diols cleavable by periodase; and dithiobis(succinimidylpropionate)(DSP), which results in thiol-cleavable disulfide bonds. The crosslinker is preferably introduced into the capture probe by (1) preparation of an alkylamine probe as described by Urdea et al. in Nucleic Acids Research 16 (11):4937-4956 (1988); (2) reaction of the free amine functionalities on the probe with the selected crosslinking agent to give probe-bound crosslinking agent; (3) purification of the probe-bound crosslinking agent using chromatographic or other means; and (4) reaction of the probe-bound crosslinking agent with a solid support having free reactive moieties, e.g., free amine groups, to provide a support-bound probe having the desired cleavage site.

The cleavage site may therefore include, for example, the following types of linkages:

The selectable cleavage site "X" in FIG. 2D may also be introduced by appropriate modification of the capture probe prior to attachment to the solid support. This method involves preparation of a polynucleotide having the structure where X is or contains the selectable cleavage site as described above. In a particularly preferred embodiment, the polynucleotide has the structure This compound may then be attached to a solid support, using conventional means well known in the art, to give the capture probe illustrated in FIG. 2D. This latter compound is prepared using a reagent derived from tartaric acid, where the 1,2-diol system is protected as the dibenzoyl compound during DNA synthesis and which further contains a dimethoxytrityl (DMT)-protected hydroxyl group and a phosphoramidite-derived hydroxyl group (wherein "iPr" represents isopropyl):

allowing for incorporation into a DNA fragment using standard phosphoramidite chemistry protocols. After synthesis and complete deprotection the DNA/DNA hybrid molecule, as noted above, contains a 1,2-diol, i.e., a linkage that can be cleaved specifically with $NaIO_4$. As will be readily appreciated by those skilled in the art, the DMT protecting group can be replaced with any suitable moiety $R^1$ that is acid-sensitive and base-stable, e.g., unsubstituted or substituted aryl or arylkyl groups, where the alkyl is, e.g., phenyl, naphthyl, furanyl, biphenyl, or the like, and where the substituents are from 0 to 3, usually 0 to 2, and include any non-interfering stable groups, neutral or polar, electron-donating or withdrawing. Similarly the phosphoramidite moiety may be replaced with other species $R^2$ including phosphorus derivatives (e.g., a phosphotriester, a phosphodiester, a phosphite, an H-phosphonate, a phosphorothioate, etc.) suitable for polynucleotide synthesis, or with hydrogen. See, for example, EP Publication No. 0225807 (Urdea et al., "Solution Phase Nucleic Acid Sandwich Assay and Polynucleotide Probes Useful Therein").

Figure 1:
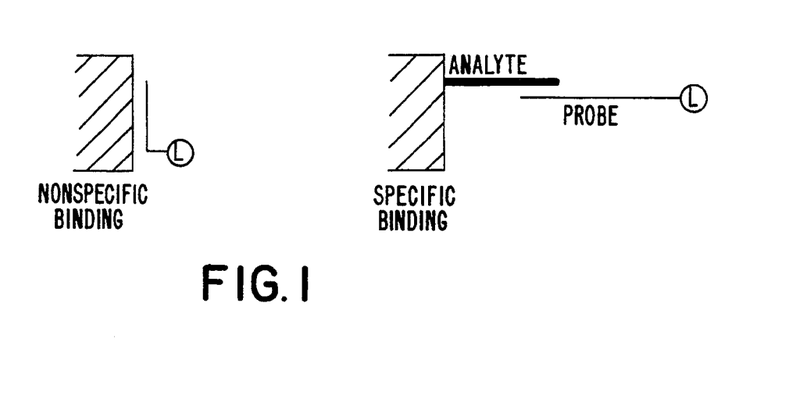
FIG. 1 illustrates the difference between specific and nonspecific binding of a label to a solid support.
Figure 2A:
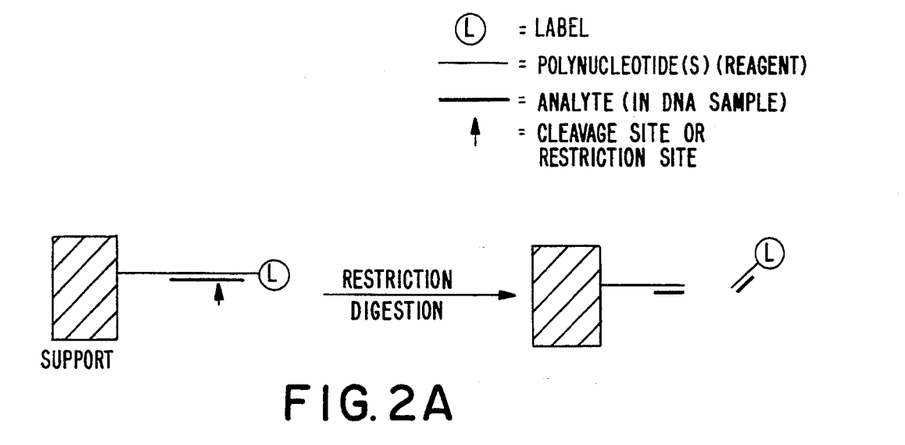
FIGS. 2A through 2D schematically illustrate the preferred method of the invention, wherein a selectively cleavable site is introduced between a support and a label through an analyte/probe complex.
Figure 2B:
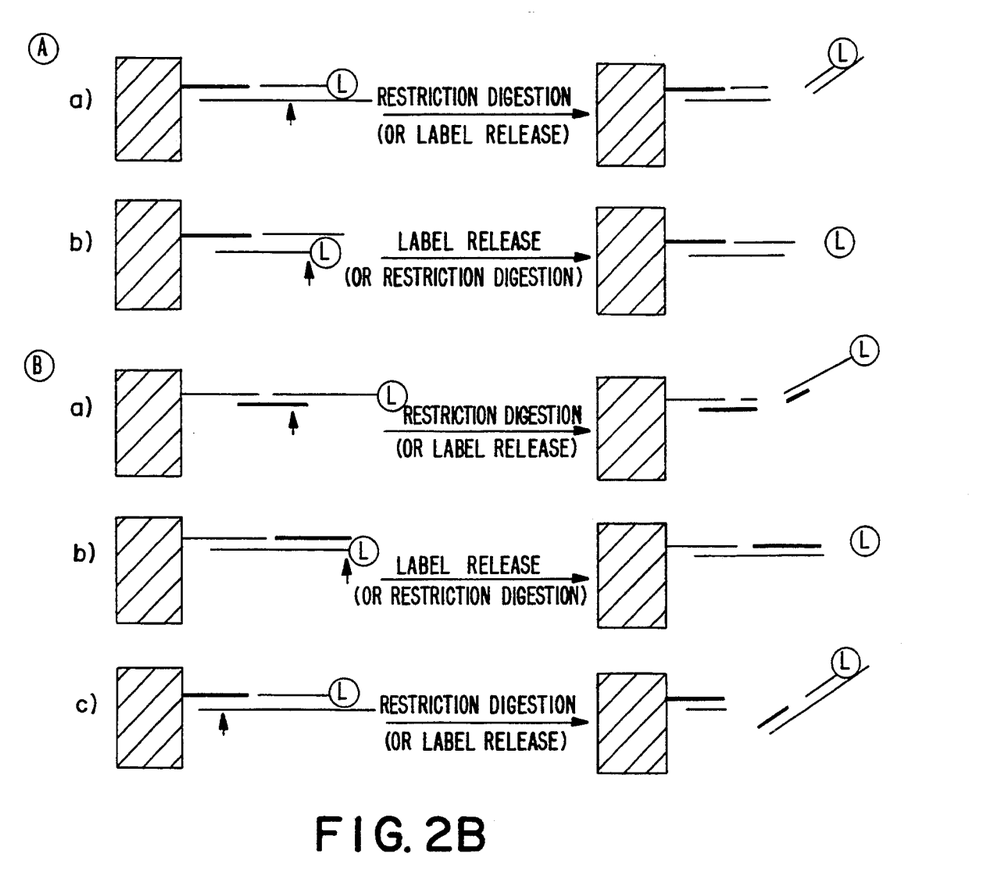
Figures 2C, 2D:
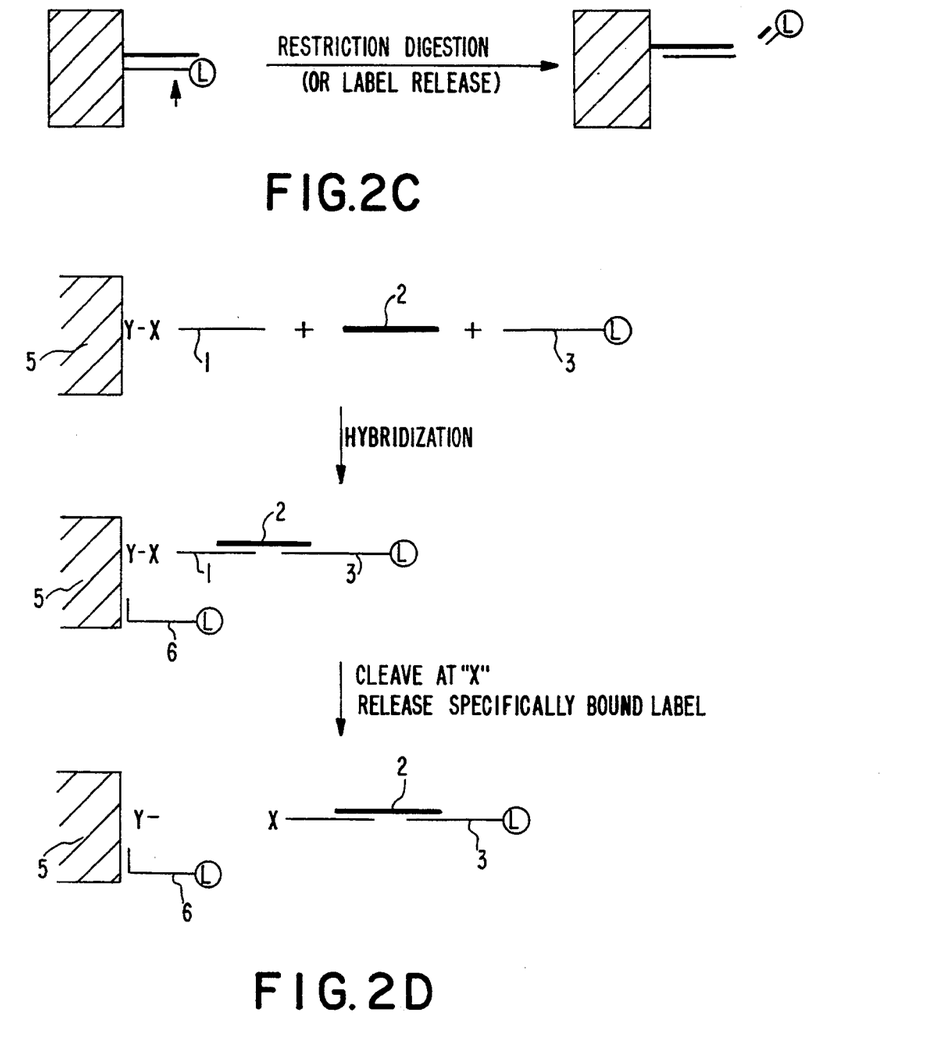

As in the embodiment represented by FIGS. 2A-2C, the embodiment of FIG. 2D enables detection of specifically bound label in solution (and thus accurate measurement of analyte 2) while nonspecifically bound label 6 remains bound to the solid suport 5.

Figure 3A:
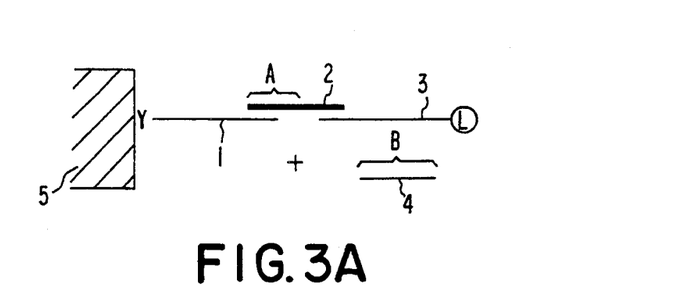
FIG. 3 schematically illustrates an alternative method of the invention, wherein specifically bound label is released through a strand replacement technique.
Figure 3B:
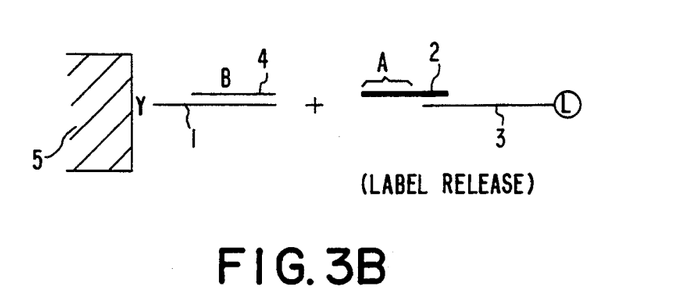

In an alternative embodiment of the invention illustrated by FIGS. 3A and 3B, a complex is formed beween a capture probe 1 (bound to solid support 5 through linkage Y), the nucleic acid analyte 2, and labeling probe 3, as in the embodiment of FIG. 2D. The procedure followed to obtain this hybridization complex is more fully described in EP Publication No. 0225807, cited supra. In order to release the specifically bound label into solution, a "replacement" polynucleotide strand 4 is introduced, selected so as to form a more stable hybrid with capture probe 1 than the analyte forms with the capture probe. Although G/C content is also a factor, this procedure typically requires that the length "B" of the replacement strand be somewhat longer than the length "A" of the duplex formed between the capture probe and the analyte.

A wide variety of supports and techniques for non-diffusive binding of oligonucleotide chains have been reported in the literature. For a review, see Meinkoth and Wahl, Anal. Biochem. (1984) 138:267-284. Supports include nitrocellulose filters, where temperatures of 80° C. for 2 hr suffices, diazotized papers, where bonding occurs without further activation, ecteola paper, etc. Agarose beads can be activated with cyanogen bromide for direct reaction with DNA. (Bauman, et al., J. Histochem. Cytochem. (1981) 29:227-237); or reacted with cyanogen bromide and a diamine followed by reaction with an α-haloacetyl, e.g., bromoacetyl or with an active carboxylic substituted olefin, e.g., maleic anhydride, to provide beads capable of reacting with a thiol functionality present on a polynucleotide chain. For example, DNA can be modified to form a χ-thiophosphate for coupling. (Pfeuffer and Hilmreich, J. Biol. Chem. (1975) 250:867-876.) It is also possible to synthesize by chemical means an oligonucleotide bound to a Teflon support and then fully deblock the material without removing it (Lohrmann, et al., DNA (1984) 3:122).

In view of the wide diversity of labels and reagents, the common aspects of the method will be described, followed by a few exemplary protocols. Common to the procedures will be hybridization. The hybridization can be performed at varying degrees of stringency, so that greater or lesser homology is required for duplexing. For the most part, aqueous media will be employed, which may have a mixture of various other components. Particularly, organic polar solvents may be employed to enhance stringency. Illustrative solvents include dimethylformamide, dimethylacetamide, dimethylsulfoxide, that is, organic solvents which at the amounts employed, are miscible with water. Stringency can also be enhanced by increasing salt concentration, so that one obtains an enhanced ionic strength. Also, increasing temperature can be used to increase stringency. In each case, the reverse direction results in reduced stringency. Other additives may also be used to modify the stringency, such as detergents.

The period of time for hybridization will vary with the concentration of the sequence of interest, the stringency, the length of the complementary sequences, and the like. Usually, hybridization will require at least about 15 min, and generally not more than about 72 hr, more usually not more than about 24 hr. Furthermore, one can provide for hybridization at one stringency and then wash at a higher stringency, so that heteroduplexes lacking sufficient homology are removed.

The nucleic acid sample will be treated in a variety of ways, where one may employ the intact genome, mechanically sheared or restriction enzyme digested fragments of the genome, varying from about 0.5 kb to 30 kb, or fragments which have been segregated according to size, for example, by electrophoresis. In some instances, the sequences of interest will be cloned sequences, which have been cloned in an appropriate vector, for example, a single-stranded DNA or RNA virus, e.g., M13.

Included in the assay medium may be other additives including buffers, detergents, e.g., SDS, Ficoll, polyvinyl pyrrolidone and foreign DNA, to minimize non-specific binding. All of these additives find illustration in the literature, and do not need to be described in detail here.

In accordance with a particular protocol, the sample nucleic acid and polynucleotide reagent(s) are brought together in the hybridization medium at the predetermined stringency. After a sufficient time for hybridization, the support will be washed at least once with a medium of greater or lesser stringency than the hybridization medium. The support with the bound polynucleotide and analyte will then be contacted with the necessary reactants (includes physical treatment, e.g., light) for cleaving the selectable cleavage site, providing for single- or double-stranded cleavage. For the most part hydrolase enzymes will be used, such as restriction endonucleases, phosphodiesterases, pyrophosphatase, peptidases, esterases, etc., although other reagents, such as reductants, Ellman's reagent, or light may find use. After cleavage, the support and the supernatant may or may not be separated, depending upon the label and the manner of measurement, and the amount of label released from the support determined.

To further illustrate the subject invention, a few exemplary protocols will be described. In the first exemplary protocol, a microtiter plate is employed, where fluorescent labeled polynucleotides are bound to the bottom of each well. DNA from a pathogen which has been cloned, is restricted with one or more restriction enzymes to provide fragments of from about 0.5–2 kb. The fragments are isolated under mild basic conditions for denaturing and dispersed in the hybridization medium, which is then added sequentially to the various wells, each of the wells having different sequences which are specifically homologous with sequences of different strains of a particular pathogen species.

The wells are maintained at an elevated temperature, e.g., 60° C., for sufficient time for hybridization to occur, whereupon the supernatant is removed and wells are thoroughly washed repeatedly with a buffered medium of lower stringency than the hybridization medium. Duplex formation results in a recognition site for a restriction enzyme common to all of the strains. To each well is then added a restriction enzyme medium for digestion of double-stranded DNAs which are digested result in the release of the fluorescent label into the supernatant. The supernatant is aspirated from each of the wells and irradiated. The amount of fluorescence is then determined as indicative of the presence of the sequence of interest. In this manner, one can rapidly screen for which of the strains is present, by observing the presence of fluorescence in the liquid phase.

In the second exemplary protocol, one employs a column containing glass beads to which are bound unlabeled polynucleotide. To the column is then added the sample nucleic acid containing DNA fragments obtained from mammalian cells. The fragments range from about 0.5 to 10 kb. The sample DNA is dispersed in an appropriate hybridization medium and added to the column and retained in the column for sufficient time for hybridization to occur. After the hybridization of the sample, the hybridization medium is released from the column and polynucleotide reagent labeled with horse radish peroxidase (HRP) through a disulfide linkage is added in a second hybridization medium under more stringent conditions than the first medium and the second medium released in the column for sufficient time for hybridization to occur. The labeled polynucleotide has a sequence complementary to the sequence of interest. The hybridization medium is evacuated from the column.

The column may then be washed one or more times with a medium of higher stringency to remove any polynucleotide sequences which have insufficient homology with the labeled polynucleotide. Ellman's reagent is then added to the column resulting in cleavage of the disulfide linkage and release of the HRP. The HRP containing medium is evacuated from the column and collected, as well as a subsequent wash to ensure that freed enzyme is not held up in the column. The resulting medium which contains the HRP label may now be assayed for the HRP label. Instead of HRP a wide variety of other enzymes can be used which produce products which can be detected spectrophotometrically or fluorometrically.

In a third protocol, the nucleic acid sample is non-diffusively bound to one end of a nitrocellulose filter by absorbing the sample with the filter and heating at 80° C. for 2 hr. The filter is washed and then added under hybridization conditions to a hybridization solution of a polynucleotide labeled with umbelliferone through an ester linkage to an alkylcarboxy substituted adenine. The labeled polynucleotide has a sequence complementary to the sequence of interest. After sufficient time for hybridization the filter is removed from the hybridization medium, washed to remove non-specifically bound nucleotides, and then submerged in a measured solution of an esterase. The rate of increase of fluorescence is monitored as a measure of the amount of analyte in the nucleic acid sample.

In another protocol, dipstick can be used of a plastic material where a holder is employed which holds a strip having a labeled polynucleotide sequenced complementary to the analyte sequence with a polyfluoresceinylated terminus. The nucleic acid sample is prepared in the appropriate hybridization medium and the dipstick introduced and hybridization allowed to proceed. After sufficient time for the hybridization to have occurred, the dipstick is removed and washed to remove any non-specific binding polynucleotide. The presence of a polynucleotide sequence of interest results in the formation of a restriction enzyme recognition site and the dipstick is then introduced into the restriction enzyme reaction mixture and digestion allowed to proceed. After sufficient time for digestion to have proceeded, the dipstick is removed, thoroughly washed, and the fluorescence in the solution read, while fluorescence above a baseline value indicates the presence of the analyte.

In another protocol, the polynucleotide reagent components are a first polynucleotide which has a sequence complementary to one region of the nucleic acid analyte and is bound to the walls of wells of a microtiter plate and a labeled second polynucleotide which has a sequence complementary to another region of the nucleic acid analyte. The label is the result of tailing the polynucleotide with $N^8$-aminohexyl deoxyadenosine triphosphate umbelliferyl carboxamide. The nucleic acid sample is introduced into the wells with an excess of the labeled polynucleotide under hybridizing conditions. After sufficient time for hybridization, the hybridization solution is aspirated out of the wells, the wells washed and the residual DNA in the wells depurinated by adding a solution of 90% formic acid and heating at 60° C. for 1 hr or adding piperidine and heating at 90° C. for 30 min.

Alternatively, the label can be a result of ligating the polynucleotide to be labeled with an excess of an oligomer obtained by treating poly-dA with chloroacetaldehyde according to Silver and Feisht, *Biochemistry* (1982) 21:6066 to produce the fluorescent $N^6$-ethenoadenosine. Release of the label is achieved with micrococcal nuclease in a solution of 100 μM $CaCl_2$ for 1 hr at 37° C.

In both instances the fluorescence of the polymer is substantially diminished due to self-quenching. Upon dissolution, a substantial enhancement in fluorescence is observed. Thus, non-specifically bound labeled polynucleotide resistant to the depolymerization would not interfere with the observed signal. Furthermore, one could measure the rate of increase of fluorescence as a quantitative measure of nucleic acid analyte, since the background fluorescent level would be low. Instead of self quenching, systems can be employed where fluorescers and quenchers alternate or in two component reagent systems, non-quenching fluorescers are present on one component and quenchers are present on the other component.

The following examples are offered by way of illustration and not by way of limitation.

EXPERIMENTAL

I. Attachment of Ribonucleotides to the 3'-end of DNA.

a. Tailing with terminal deoxynucleotide transferase (TdT).

The following is a modification of the method described by R. Roychoudry, *Method in Enzymology* (1980) 65:43. A synthetic oligonucleotide of the composition (5' to 3') ATTCGACGCTTATGG (fragment 1) was tailed with rATP. To a solution of 4005 pmoles of fragment 1 (based on 20 $OD_{260}$ units per mg) in 15 μl of 0.83 mM ATP, 2.5 μl of 10× TdT buffer (1.4M potassium cacodylate, 0.6M Tris pH 7.6, 10 mM $CoCl_2$, 1 mM dithiothreitol (DTT)), 2 μl of TdT (calf thymus, P-L Biochemicals, Inc.; 13.5 units) is added. The 24.5 μl sample was left for 1 hr at 37° C., the evaporated to dryness. The pellet was dissolved in 10 μl of 90% formamide, 0.05% bromophenol blue, 1% Ficoll, heated to 90° C. for 5 min and loaded on a 20% denaturing polyacrylamide gel run at 40 ma. A band corresponding to fragment 1 extended by one riboadenosine unit was visualized by U.V. shadowing, cut from the gel and eluted overnight in 0.1M Tris borate pH 8.0, 5 mM EDTA, 0.5 m NaCl (Maxam and Gilbert, *Methods in Enzymology* (1980) 65:499–560). Desalting was achieved with a C-18 SEP-PAK (Waters Associates) as follows: The cartridge was first washed with 5 ml of reagent grade methanol then 10 ml of distilled water. The filtered sample was then applied by syringe to the SEP-PAK. After washing with 20 ml of water, the DNA was eluted with 3 ml of 1:1 (V:V), triethylamine acetate, pH 7.3:methanol. The solution was then evaporated to dryness (yield ~80%).

b. Ligation with $T_4$ ligase.

The following process was used to produce a 137 base fragment that contained a 3'-terminal riboadenosine. Fragment 1 from above is used as a "universal" adaptor in order to produce by ligation a ribonucleotide tailed DNA sequence.

Fragment 2

AGTTGGCAGTACAGCCTAGCAGCCATG-
GAAACGATGTATATTTCCGCGAGAGGAC-
GACAG

Fragment 3

GGTCGTCCGCGGGATTCAGCGCCGACG-
GGACGTAAACAAAGGACGTCCCGCGAAG-
GATCC

Fragment 4

TTCCATGGCTGCTAGGCTGTACTG-
CCAACTGGATCCTTCGCG-
GGACGTCCTTTGTTTACG

Fragment 5

AATTCTGTCGTCCTCTCGCG

Fragment 6

CCATAAGCGTCG

All sequences unless otherwise indicated were 5', 3' hydroxyl. The sequences can be ligated as follows:

1) ligation
2) gel isolation

Fragment 2 was 5' phosphorylated with $T_4$ polynucleotide kinase. To 900 pmoles of the fragment that had been evaporated to dryness were added 2 μl of 10× KB-TS (500 mM Tris, 100 mM $MgCl_2$, 10 μg/ml spermidine), 2 μl 10 mMATP, 2 μl 10 mM DTT, 1 μl (8 units) $T_4$ kinase (New England Nuclear) and 13 μl of water. After 30 min at 37° C., another 8 U of $T_4$ kinase were added. After an additional 30 min at 37° C., 45 μl (990 pmoles) of fragment 1 that had previously been 5'-phosphorylated in a similar manner were added. After adding 22 μl of 2M sodium acetate and 8 μl of 250 mM EDTA, the solution was heated for 5 min at 65° C. to inactivate the $T_4$ kinase. Fragments 3 through 6 were then added (2.6 μl, 902 pmoles; 8 μl, 1008 pmoles; 32 μl, 1003 pmoles, 45 μl, 936 pmoles, respectively). The solution was vortexed, 680 μl of cold ethanol were added and the solution was placed at −80° C. for 20 min. The pellet was then centrifuged at 12,800 RPM for 10 min, decanted, washed with cold ethanol twice and dried.

To anneal the pieces, 18 μl of water were added to dissolve the pellet, the mixture heated in added to dissolve the pellet, the mixture heat in boiling water and cooled to room temperature slowly (~10 min). At this point were added 3 μl of 10×KB-TS, 3 μl of 10 mM ATP and 3 μl of T4 DNA ligase (New England Biolabs; 40,000 units per ml). After 30 min at 14° C., the solution was dried and purified on a 10% denaturing polyacylamide gel as described above for fragment 1. (Yield ~75 pmoles.)

c. Synthesis of DNA on a 2'-nitrobenzyluridine control pore glass support.

The 5'-dimethoxytrityl 2'-nitrobenzyluridine derivative of control pore glass (long chain alkylamino; Pierce Chemical Company) was prepared by Cruachem, Bend Oregon, according to Gough, et al., *Tetrahedron Lett.* (1981) 22:4177. Oligonucleotide synthesis was carried out on an automatic synthesizer (Warner et al., *DNA* 3, in press).

The 2'-nitrobenzyl functionality was removed by U.V. irradiation as described by Ohtsuka, et al., *Nucleic Acids Res.* (1974) 1:1351, except that a 2100 watt mercury bulb was employed. Five min irradiation in a pyrex cuvette was used for all samples (~14.5 μmoles of 2'-nitrobenzyluridine).

A sequence corresponding to 5' TTCCATGGCTG-CTAGGC TGTACTGCCAACT-GGATCCTTCGCGGGACGTCCTTTGTTTAC-GrU 3' (fragment 7) was produced in this manner and used for the coupling described below.

II. Attachment of DNA by the 3' end to solid supports a. Synthesis of thiosemicarbazido control pore glass (TSC-CPG).

Isothiocyanate control pore glass (Pierce Chemical) was modified with hydrazine to yield the thiosemicarbazido derivative as follows. 400 mg of isothiocyanate CPG was placed in a 50 ml round bottom flask. 25 ml of dimethylsulfoxide, 200 μl of distilled pyridine and 500 μl of a 0.6% hydrazine in dimethylsulfoxide solution were added (see, for example, J. Bauman, et al., *J. of Histochem. and Cytochem.* (1981) 29:227). After 18 hr with occasional mixing in the dark, the support was washed with 50 ml each of dimethylsulfoxide, pyridine, methanol and 2 L of 0.01M Tris, pH 7.5.

b. Attachment of fragment 7 to the solid support.

Approximately 2000 pmoles of fragment 7 was dried from water by evaporation. To this was added 100 μCi of $\chi^{32}$P-ATP (New England Nuclear), 2 μl of 10×KB (0.5M Tris HCl pH 7.8, 100 mM MgCl$_2$, 100 mM DDT), 1 μl (8U) T4 kinase (New England Nuclear). After 30' at 37° C., the solution was diluted to 1 ml with gel elution buffer and SEP-PAK de-salted as described above. Fragment 7 (20 μl, 982 pmoles) was treated with 20 μl of 1 mM sodium periodate (Sigma) in 0.01M Tris-HCl, pH 8.0 for 1 hr at 0° C. in the dark. To this was added 10 mg of TSC-CPG in 100 μl of 0.1M sodium acetate, pH 5.6 and the mixture allowed to set for 1 hr at 0° C. in the dark, and then at 4° C. overnight.

In order to block the remaining thiosemicarbazido functionalities, periodate oxidized ATP was used. A 20 μl sample of 100 mMATP was treated with 20 mg of sodium periodate in 100 μl of 0.01M Tris-HCl, pH 8.0. After 1 hr in the dark, 45 μl of the solution was added to the 10 mg of fragment 7-TSC-CPG in 150 μl of 0.1M sodium acetate. After 6 hr at 4° C., the support was washed extensively with 4× standard sodium citrate (SSC).

Based on the incorporated counts, 13% of fragment 7 (128 pmoles) were attached to the glass support.

III. Attachment of 5' ends of DNA to solid supports a. Preparation of bromoacetyl control pore glass (BA-CPG).

Synthesis of O-bromoacetyl N-hydroxysuccinimide was carried out approximately as described by Cuatreacasas, *J. Biol. Chem.* (1974) 245:3059.

A mixture of 347 mg of bromoacetic acid and 345 mg of N-hydroxysuccinimide (Sigma) was made up in 20 ml of distilled dioxane. To this mixture was added 532 mg of dicyclohexylcarbodiimide. After 70 min of shaking at room temperature, the cloudy solution was filtered through glass-wool.

To 500 mg of long chain alkylamino control pore glass (Pierce Chemical; 0.1 meq/g) was added 10 ml of 0.10M sodium phosphate, pH 7.6. The slurry was placed on ice and the O-bromoacetyl N-hydroxysuccinimide solution was slowly added. After 30' with occasional stirring, the BA-CPG was washed with 5 L of 0.1M NaCl.

The number of equivalents of bromoacetate on the support was determined with a 5',5'-dithiobis(2-nitrobenzoic acid) acid (DTNB) test (Butterworth, et al., *Arch. Biol. Biophysl.* (1967) 118:716). Stock solutions containing 200 mg of DTNB in 50 ml of water and 114 mg of 2-mercaptoethylamine in 100 ml of water were prepared. BA-CPG (10 mg) was reacted with 10 μl of the 2-mercaptoethylamine solution plus 500 μl of 0.05M sodium phosphate at pH 8.0 for 10 min at room temperature. The solution was then tested with 100 μl of DTNB and the visible spectrum was recorded (E=1.36×10 mol$^{-1}$cm$^{-1}$ at pH 8). A control was run with 2-mercaptoethylamine without BA-CPG. From the amount of 2-mercaptoethylamine lost upon treatment with BA-CPG, it was determined that BA-CPG contained 10 mmoles bromoacetate per mg.

b. 5' attachment of DNA to BA-CPG.

To 10 μl (333 pmoles) of fragment 3 (see above) was added 10 μl of 3-$^{35}$S-ATP (adenosine 5'-0-(3-thiotriphosphate; 0.25 mCi, New England Nuclear)), 2–5 μl of 10×KB and 1 μl (8U) of T4 polynucleotide kinase. After 30 min at 37° C., 1 μl of 50 mM 3-S-ATP (lithium salt; P.-L. Biochemicals) and 1 μl (SU) T4 kinase were added. After an additional 30 min at 37° C., the fragment was gel isolated as described above (yield 266 pmoles). Samples were counted on a Beckman LS7000 liquid scintillation counter in Atomlite (New England Nuclear).

A 5 mg sample of BA-CPG was washed by centrifugation 3 times with water and 2 times with 0.10M sodium phosphate, pH 7.6. The 5'thiophosphate fragment 2 was dissolved in 100 μl of the phosphate buffer and added to the washed BA-CPG. The slurry was mixed by rotation on a rotary evaporator for 2 hr at room temperature. The solution was decanted and discarded. In order to block the remaining bromoacetate functionalities, the support was treated with 200 μl of 50 mM sodium phosphate, pH 8.0 and 50 μl of 2-mercaptoethanol for an additional 2 hr. Subsequently the solution was decanted and the support was extensively washed with 4XSSC (yield ~10 pmoles per mg of CPG).

IV. Synthesis of Horseradish Peroxidase-DNA Conjugates a. Purification by Elutip.

Horseradish peroxidase (HRP) (2 mg; Type VI, Sigma; 10,000U/38 mg) was dissolved in 0.5 ml of 0.1M sodium phosphate buffer, pH 7.5. O-bromoacetyl N- hydroxysuccinimide (15 μl) was added to the above solution and reaction allowed to proceed for 30 min at room temperature. The solution was passed over a PD-10 Sephadex G-25M column (Pharmacia) that had previously been equilibrated with 30 ml of 0.1M sodium phosphate, pH 7.5. The brown fraction (1–1.2 ml) was collected. Fragment 8 (5' to 3', GGTATTGTT-GAACAATGTTGTACTTCTATTTG) that had previously been 5'-thiophosphorylated with 3'-$^{35}$S-ATP as described above and dried (30 pmoles) was taken up in 50 μl of the phosphate buffer. To this thiophosphorylated fragment 8 solution was added the functionalized HRP and the mixture allowed to set for 30 min at room temperature. The mixture was passed over an Elutip-d (Schleicher and Schuell) column. The peroxidase-DNA conjugate is eluted in the void volume (26% of the counts were recovered). A control experiment conducted as described above but using 5'-$^{32}$P-phosphate labeled fragment 8 showed less than 0.5% of the counts were eluted under these conditions.

b. Separation by gel.

A peroxidase conjugate of fragment 9 (5' to 3', TTGAAGAACTACGGTTTGTTGTCTTGTTT-CAGAAAGGACTTGCACAAGACCCAAACC) was produced as above except that 360 pmoles of bromoacetyl horseradish peroxidase was combined with 156 pmoles of fragment 9 in 120 μl of 0.025M sodium phosphate, pH 7.5. Instead of passing over an Elutip-d column, the mixture was evaporated to dryness, suspended in 1 μl of 75% glycerol, 10 μl of H$_2$O and 1 μl of 1% bromophenol blue. This material was then run on a 10% native protein gel. (Lindle, et al., *Methods in Enzymol.* (1983) 92:309). A control experiment with 5'-$^{32}$P-phosphate fragment 9 was also run. The enzyme-DNA conjugate was well resolved from the unconjugated peroxidase as a faster running $^{35}$S-labeled species. The gel was stained with 100 ml of 10 mM Tris-HCl, pH 7.5, 50 mM NaCl, 60 μl of 30% H$_2$O$_2$ to which was added 60 mg of 4-chloro-1-naphthol dissolved in 20 ml of cold methanol. Since this stain is based on the horseradish peroxidase activity, it was possible to show that the peroxidase-DNA conjugate was itself active. No new active species was produced with the $^{32}$P-fragment 9 control.

c. Hybridization of DNA-peroxidase to complementary DNA.

5'-Thiophosphorylated fragment 11 (5' to 3', CCAA-GAGCTGGTCAAATCTTGAAGCAAACCTAC-GACAAGTTCGACACCAACATG AGATCT-GACGACGCTTTG) was $^{32}$P-labeled as above. A 10% excess of fragment 12 (with reference to fragment 11) was added to the reaction mixture of 5'-thiophosphate fragment 11 plus bromoacetyl peroxidase. The solution was heated to 60° C. for 3 min and cooled to room temperature. A control was performed with fragment 12 plus bromoacetyl enzyme without 5'-thiophosphate fragment 11. A gel was run as before and the reaction mixture of fragment 11 plus bromoacetyl enzyme was run as a standard. The lane of fragment 12 plus enzyme and fragment 11 revealed a new slower running band (relative to the fragment 11-peroxidase conjugate) that contained $^{32}$P label. This band was also positive for peroxidase activity. No enzyme positive-$^{32}$P labeled band was found for the fragment 12-peroxidase control.

V. Assay

The fragments in this assay represent a model system and comprise a portion of the Hepatitis B virus genome extending about 60 bases in the 5'- (fragment 3) and 3'-direction (fragment 2) from the BamHI site at base No. 1403 of HBV DNA. The analyte, fragment 4, is complementary to the 3' end of fragment 3 and the 5' end of fragment 2. The solid-supported fragment 3 was produced as described in Section IIIb. Fragment 2 was 5' labeled with χ$^{32}$P-ATP according to the initial part of Section IIb (as applied to fragment 7).

a. Hybridization, Probe Capture.

Approximately 3 pmoles of a suspension of solid-supported fragment 3 (0.3 mg) and 5 pmoles of $^{32}$P-fragment 2 (in 10 μl H$_2$O) were used in each experiment. Appropriate quantities of reagents (see Table 1 below) were added to give a final volume 50–100 μl, heated to 90° C. and cooled to room temperature over a 1 hr period. After washing with 4×SSC at room temperature, samples of the solid support were Chernenkov counted on a Beckman LS7000 liquid scintillation counter.

TABLE 1

|   | pmole of Fragment 4, μl | μl of 20 × SCC | μl H$_2$O | CPM Bound |
|---|---|---|---|---|
| A | 0,0 | 8 | 20 | 31,260 |
| B | 1,10 | 8 | 10 | 132,293 |
| C | 0.5,5 | 8 | 15 | 113,039 | b. Restriction Cleavage Release.

Typically, the solid support after probe-capture as described above is washed with BamHI buffer (20 mM Tris-HCl), pH 8.0, 7 mM MgCl$_2$, 100 mM NaCl, 2 mM 2-mercaptoethanol) twice and resuspended in 20 μl of the same buffer. To this 1 μl of BamHI (BRL; 5000 Units/715 μl) is added and mixed. After 30 min incubation at 37° C. the supernatant and one water wash are removed from the tube containing the settled solid support and counted. An additional 20 μl of buffer and 2 μl of enzyme are then added and left overnight at 37° C. The supernatant and one water wash are counted as before. Controls without enzyme are also run.

TABLE 2

|   | Initial CPM on Support | CPM released after 30 min | CPM released after 18 h |
|---|---|---|---|
| Sample 1 w/enzyme | 69660 | 2064 | 10513 |
| Sample 1 w/o enzyme (control) | 67353 | 536 | 2524 |
| Sample 2 w/enzyme | 34982 | 1848 | 6336 |
| Sample 2 w/o enzyme (control) | 44113 | 504 | 2191 |

VI. Preparation of PCL (Periodate-Cleavable Linker)

O,O-Dibenzoyl tartaric acid monohydrate (18.8 g, 50 mmole) was dissolved in 250 ml CH$_3$CN and the solvent was removed in vacuo. This process was repeated. The resulting oil was dissolved in 250 ml THF and dicyclohexylcarbodiimide (DCC) (10.6 g, 50 mmole) dissolved in 50 ml THF was added. A precipitate started forming in a few minutes. After stirring for 18 hr at 20° C. the reaction mixture was filtered, and the precipitate washed with a little THF. The precipitate was then dried in high vacuum to give 10.8 g (100%, 50 mmole) dicyclohexylurea (DCHU). To the combined filtrate was added 2-(N-methyl)aminoethanol (4.0 ml, 50 mmole) and the reaction mixture was stirred for 1 hr at 20° C. Then, DCC (10.6 g, 50 mmole) in 50 ml THF was added; a small precipitate was formed. After about 1 hr, 2-(N-methyl)aminoethanol (4.0 ml, 50 mole) was added and the reaction mixture stirred for 18 hours at 20° C.

The formed precipitate was filtered often and washed with a little THF. The dried precipitate of DCHU weighed 10.8 g (100%). The combined filtrate was evaporated to an oil; chromatography on silica afforded 8 g (17 mmole) O,O-dibenzoyl tartaric di(N-methyl-2-hydroxyethyl)amide (1). The product was eluted with 6% MeOH/$CH_2Cl_2$.

To (1) (8.6 mole) in 50 ml $CH_2Cl_2$ containing dimethylamino pyridine (DMAP) (0.11 g) and triethylamine (TEA) (2.4 ml) was added dropwise, DMT-Cl (8.6 mmole) dissolved in 50 ml $CH_2Cl_2$. After addition of DMT-Cl, the reaction mixture was stirred for 1 hr at 20° C., and the solvent was removed by evaporation. The residue was dissolved in 600 ml ethyl acetate and the organic phase washed with 400 ml 5% NaHCO and 400 ml 80% saturated aqueous NaCl. The organic phase was dried over solid $Na_2SO_4$. After 30 min, the $Na_2SO_4$ was filtered off, and the supernatant was concentrated to an oil and then coevaporated with toluene and $CH_3CN$.

The crude material was subjected to silica gel chromatography using n-butanol/$CH_2Cl_2$ for elution. The pure mono-DMT product eluted with 2-3% n-butanol/$CH_2Cl_2$ to give 1.53 g (2 mmole) of O,O-dibenzoyl tartaric 2-(O-dimethoxytrityl)hydroxyethyl-N-methyl,N-methyl-2-hydroxyethyldiamide.

This material was dissolved in 20 ml $CH_2Cl_2$ containing diisopropylethylamine (DIPEA) (3 mmole). After cooling to 10° C., 2.2 mole methoxy-N N-diisopropylamino chloro phosphine was added under argon. After 15 min, ethyl acetate was added, and the organic phase washed with 80% saturated aqueous NaCl, dried over solid $Na_2SO_4$, and evaporated to dryness. After coevaporation with toluene and dry $CH_3CN$, the residue was dissolved in 10 ml dry $CH_3CN$. This solution was aliquoted into 19 dry Weaton vials and the solvent removed in vacuo. The vials were closed with septum screw caps and stored at −20° C.

The DMT-PCL-phosphoramidite was coupled to oligonucleotides using standard techniques. The following oligonucleotide was synthesized:

In the foregoing structure, "PCL" represents the periodate-cleavable linkage

"BLA3c" represents the nucleotide sequence (5' to 3') GATGTGGTTGTCGTACTT, and "T.LLA2.TT" represents the nucleotide sequence (5' to 3') TTGA-CACGGGTCCTATGCCTAAT. After complete deprotection the oligonucleotide was purified by PAGE, the product band excised, eluted with MG buffer and desalted using a SEP-PAK ® cartridge as described by Sanchez-Pescador et al., DNA 3:339-343 (1984).

Degradation was performed as follows:

~0.6 OD purified material in 6 λ $H_2O$ was treated with 50 λ0.1M Na·$IO_4$ and left for 1 hr at 20° C. 0.4 ml of a solution of glycerol in $H_2O$ (1λ°/ml) was added. The combined solution was passed through a PD-10 column (Sephadex G25), equilibrated with 0.1M triethylammonium acetate (TEAA) and eluted with the same buffer. 0.5 ml fractions were collected and pooled, and the solvent removed in a Speed-Vac. Analysis by 15% PAGE showed complete degradation of starting material into two new bands of the expected sizes.

VII. Sodium Periodate Release

A. A $^{32}$P-labeled probe was prepared as described by Urdea et al. in *Nucleic Acids Research* 16 (1988), cited in the preceding section. The probe had the sequence (5' to 3') AAGTACGACAACCACATCGGAT-GACCTCGGATCGA CCT*T-$^{32}$P where * is the modified nuleotide represented by the structure as described in EP Publication No. 0225807, supra. A synthetic oligonucleotide having the sequence (5' to 3') GATGTGGTTGTCGTACTTCTTCTTT-GGAGAAAGTGGTG was used as analyte. Microtiter capture wells were prepared using two different probes: (1) *CACCACTTTCTCCAAAGAAG (designated XT1*1ca in Table 3, below); and (2) *TT-X-CACCACTTTCTCCAAAGAAG (* representing the alkylamine nucleotide above), where X represents the periodate-cleavable linkage as described in the preceding section, using the following procedure. The wells were prepared from the Immulon II strips by adding, to each well, 200 μl of a 200 μg/ml solution of polyphenylalanyl-lysine (Sigma Chemical Inc.) in water. The covered strips were left at room temperature for 30 min to 2 hr, then washed as above. A 10 $OD_{260}$ sample of the oligonucleotide of 3B above in 60 μl of 1×PBS was treated with 140 μl of DMF containing 10 mg of ethylene glycolbis(succinimidylsuccinate) (Pierce Chemicals Inc.). The mixture was vortexed and incubated in the dark at room temperature. After 15 min, the solution was passed over a Sephadex G-25 column (PD-10 from Pharmacia), previously equilibrated with 30 ml of 1×PBS. The void volume of the column was diluted to a final volume of 35 ml with 1×PBS. To each well, a 50 μl aliquot of the capture probe solution was added. After covering with plastic wrap, the wells were incubated at room temperature in the dark for 30 min to overnight. The wells were not overcoated with hybridization mix.

Stock solutions containing 1 fmole, 100 amoles and 10 amoles of the analyte fragment were prepared in a hybridization buffer containing 4× SSC. A control solution was similarly prepared, containing no analyte. Four sets of wells were then set up. To each well was added 40 µl of the selected solution, i.e., containing either 1 fmole, 100 amoles, 10 amoles or no analyte. Hybridization was carried out at 55° C. in a water bath for 1 hr. Tubes were capped and wells were sealed with an adhesive Linbro/Titertek membrane. After washing twice with 380 µl of 4× SSC, an additional 40 µl of 4× SSC containing 10 fmoles of $^{32}$P-labeled probe was added. The wells were incubated for 1 hr, at 37° C., at which point they were again washed twice with 380 µl of 4× SSC.

Total counts $^{32}$P were then evaluated using an LKB 1214 Rackbeta scintillation counter. Results are set forth under "Total Counts" in Table 3.

To one set of wells containing the periodate-cleavable polynucleotide and one set of wells containing XT1*1ca solution was added 100 µl of 100 mM NaIO$_4$ in 4× SSC. The wells were incubated at room temperature for one minute. The periodate solution was transferred to clean wells and counted. Results are set forth in the columns entitled "100 mM NaIO$_4$" and "4× SSC" in Table 3.

As a control, 100 µl of 4× SSC was added to one set of wells containing the periodate-cleavable polynucleotide. The wells were then incubated at room temperature for one minute and the solution was transferred to clean wells. The transferred solution was counted and results are tabulated under the heading "XT1*1ca wells" in Table 3.

TABLE 3

| Analyte Amount | Total Counts | 100 mM NaIO$_4$ | 4X SSC | XT1*1ca wells |
| --- | --- | --- | --- | --- |
| 1 fm | 8378.80 | 563.49 | 71.79 | 53.84 |
| | 3440.30 | 465.74 | 29.91 | 43.87 |
| | 3368.20 | 638.29 | 23.93 | 41.88 |
| 100 am | 3130.60 | 53.84 | 43.87 | 57.83 |
| | 5661.70 | 66.81 | 82.76 | 48.87 |
| | 3068.50 | 47.86 | 26.92 | 23.93 |
| 10 am | 3119.60 | 17.94 | 36.89 | 35.90 |
| | 7161.20 | 52.85 | 54.84 | 36.9 |
| | 2408.61 | 20.94 | 17.94 | 34.9 |
| zero | 3133.49 | 34.90 | 129.64 | 32.91 |
| | 5729.60 | 38.89 | 22.93 | 43.88 |
| | 3613.92 | 14.95 | 32.90 | 58.84 |

| | S/N Ratios: | |
| --- | --- | --- |
| | No Release | Release |
| 1 fmole | 1.2 ± 0.8 | 18.8 ± 8.6 |
| 100 amoles | 1.0 ± 0.5 | 1.9 ± 0.9 |
| 10 amoles | 1.0 ± 0.7 | 1.0 ± 0.8 |

B. In a second experiment, the aforementioned procedure was repeated with the following variations: (1) the probe used was a $^{32}$P-labelled 19-mer having the sequence *CGTGTCAGGCATAGGACC (5' to 3', * as above); (2) the "analyte" was a synthetic oligonucleotide having the sequence GGTCCTATGCCTGACACGCTTCTTTGGAGAAAGTGGTG; (3) one analyte concentration was evaluated rather than three (1 fmole); and (4) 100 fmoles rather than 10 fmoles $^{32}$P-labelled probe were used. Results are summarized in Table 4.

TABLE 4

| Analyte Amount | Total Counts | 100mM NaIO$_4$ in 4X SSC | 4X SSC |
| --- | --- | --- | --- |
| 1 fm | 1885.95 | 582.44 | 93.97 |
| | 1963.40 | 581.44 | 97.72 |
| | 2130.60 | 346.05 | 119.66 |
| | 1877.20 | | |
| | 1692.90 | | |
| | 1666.98 | | |
| zero | 710.60 | 50.85 | 64.81 |
| | 762.70 | 36.89 | 39.88 |
| | 731.60 | 31.91 | 55.84 |
| | 1030.35 | | |
| | 554.52 | | |
| | 892.67 | | |

| | S/N Ratios: | |
| --- | --- | --- |
| | No Release | Release |
| 1 fmole | 2.40 ± 0.55 | 12.6 ± 4.59 |

VIII. Strand Replacement

An alkaline phosphatase probe was prepared as described by Urdea et al., Nucleic Acids Research 16, supra. The probe had the sequence (5' to 3') AAGTACGACAACCACATCGGATGACCTCGGATCGACCT*T with * as above. A synthetic oligonucleotide having the sequence (5' to 3') GATGTGGTTGTCGTACTTCTTCTTTGGAGAAAGTGGTG was used as analyte. A second synthetic oligonucleotide was prepared having the sequence CTTCTTTGGAGAAAGTGGTGTTCATAGAGAAACGATAT ATAGAGACACGATATAGGGATA and was used as the specific release strand, i.e., the replacement strand enabling label release as discussed above. Plates were made using an oligonucleotide having the sequence *TATCCCTATATCGTGT CTCTATATATCGTTTCTCTATGAACACCACTTTCTCCAAAGAAG as capture probe. Wells were prepared as described in the preceding section, except that Microlite I wells (Dynatech) were used and, after the final incubation step, the wells were washed with 1× PBS, then coated with H buffer, and washed again.

Three sets of capture wells were set up, each set having an analyte-containing well and a control well, i.e., containing no analyte. To each well was added 40 µl 4× SSC with either 1 fmole or no analyte. Hybridization was carried out at 55° C. for 1 hour. After washing twice with 380 µl of 4× SSC, 40 µl of 4× SSC containing 100 fmoles of alkaline phosphatase probe were added to the wells. The wells were incubated at 37° C. for 1 hr, at which point washing was carried out (1) twice with 380 µl of buffer containing 0.1× SSC and 0.1% SDS, and (2) twice with 380 µl of 4× SSC.

Alkaline phosphatase activity was measured by incubation of the samples with dioxetane, a chemiluminescent substrate. Luminescence was recorded using a microtiter dish reading luminometer (Dynatech).

To one set of wells, 20 µl 4× SSC were added, followed by incubation at 37° C. for 1 hr. 20 µl dioxetane were added, and the wells were again incubated at 37° C. for 1 hr. Alkaline phosphatase activity was measured, and results are set forth in Table 5 under the heading "No Transfer".

20 µl 4× SSC were added to a second set of wells, which were then incubated at 37° C. for 1 hr. The individual solutions were transferred to Microlite I wells, and 20 µl dioxetane was added. The wells were again incubated at 37° C. for 1 hr. Alkaline phosphatase activity was measured as above, and results are tabulated in Table 5 under "SSC Release".

20 μl 4× SSC were added to the third set of wells containing 30 pmoles specific release oligonucleotide. The wells were incubated at 37° C. for 1 hr, and the solutions were then transferred to Microlite I wells. 20 μl dioxetane were added, and the wells were again incubated at 37° C. for 1 hr. Alkaline phosphatase activity was measured as above, and results are set forth in Table 5 under "Oligo Release".

TABLE 5

| Analyte Amount | No Transfer | SSC Release | Oligo Release |
|---|---|---|---|
| 1 fm | 16.26 | 0.47 | 9.52 |
|  | 14.66 | 0.56 | 9.89 |
|  | 15.76 | 0.55 | 10.42 |
| zero | 0.33 | 0.04 | 0.08 |
|  | 0.33 | 0.04 | 0.05 |
|  | 0.28 | 0.04 | 0.07 |
| S/N Ratios: | | | |
| 1 fmole | 49.66 ± 5.27 | 13.17 ± 1.23 | 149.15 ± 34.84 |

B. The experiment of Section VIII A was repeated, with results set forth in Table 6.

TABLE 6

| Analyte Amount | No Transfer | SSC Release | Oligo Release |
|---|---|---|---|
| 1 fm | 11.82 | 0.20 | 4.05 |
|  | 12.39 | 0.18 | 5.02 |
|  | 12.72 | 0.19 | 4.79 |
| zero | 0.98 | 0.07 | 0.10 |
|  | 1.09 | 0.06 | 0.11 |
|  | 1.11 | 0.08 | 0.10 |
| S/N Ratios: | | | |
| 1 fmole | 11.6 ± 0.88 | 2.7 ± 0.4 | 46.2 ± 6.9 |

It is evident from the above results, that the subject method provides for a simple, rapid and accurate approach for detecting specific polynucleotide sequences from diverse sources. The method provides for high sensitivity and great flexibility in allowing for different types of labels which involve detectable signals which have been employed in immunoassays. Thus, the subject method can be readily adapted to use in conventional equipment for immunoassays which are capable of detecting radioactivity, light adsorption in spectrophotometers and light emission in fluorometers or scintillation counters. The subject method is applicable to any DNA sequence and can use relatively small probes to reduce false positive and minimize undesirable heteroduplexing. By cleavage of the label from the support for measurements, background values can be greatly reduced, since the reading can occur away from the support. Also, there is a further redirection in background due to the necessity to cleave the label from the polynucleotide chain. The subject method can therefore provide for the accurate and economical determination of DNA sequences for diagnosing disease, monitoring hybrid DNA manipulations, determining genetic traits, and the like.

Although the foregoing invention has been described in some detail by way of illustration and example for purposes of clarity of understanding, it will be obvious that certain changes and modifications maybe practiced within the scope of the appended claims.

What is claimed is:

1. A DNA probe useful for detecting the presence of an oligonucleotide containing a sequence of interest, comprising a polydeoxyribonucleotide reagent bound proximal at one end to a support and at its opposite end having a sequence complementary to said sequence of interest, wherein a selectable cleavage site X is present within the polynucleotide reagent, and further wherein the selectable cleavage site X (a) is chemically cleavable; (b) is other than a restriction enzyme cleavable site; (c) is other than a phosphodiester linkage; and (d) provides for a complete break between adjacent nucleotides in the polynucleotide reagent upon cleavage.

2. A polynucleotide reagent having the structure wherein $DNA_1$ is a first strand of DNA, $DNA_2$ is a second strand of DNA, and X comprises a selectable cleavage site which: (a) is chemically cleavable; (b) is other than a restriction enzyme clearable site; (c) is other than a phosphodiester linkage; and (d) provides for a complete break between adjacent nucleotides in the reagent upon cleavage.

3. The polynucleotide reagent of claim 2, wherein X comprises a linkage cleavable by a reagent selected from the group consisting of $OH^-$, hydroxylamine, $SH^-$, or periodate.

4. The polynucleotide reagent of claim 2, wherein X comprises a linkage selected from the group consisting of

5. The polynucleotide reagent of claim 2, wherein X contains the moiety

6. The polynucleotide reagent of claim 2, wherein X is

7. A reagent useful in polynucleotide synthesis, having the structure wherein $R^1$ is an acid-sensitive, base-stable protecting group, and $R^2$ is selected from the group consisting of H, phosphoramidite, phosphotriester, phosphodiester, phosphite, H-phosphonate, and phosphonothioate.

8. The reagent of claim 7, wherein $R^1$ is DMT and $R^2$ is where iPr is isopropyl.

9. The polynucleotide reagent of claim 3, wherein X is cleavable by $OH^-$.

10. The polynucleotide reagent of claim 3, wherein X is cleavable by hydroxylamine.

11. The polynucleotide reagent of claim 3, wherein X is cleavable by $SH^-$.

12. The polynucleotide reagent of claim 3, wherein X is clearable by periodate.

13. The polynucleotide reagent of claim 9, wherein X comprises

14. The polynucleotide reagent of claim 9, wherein X comprises

15. The polynucleotide reagent of claim 10, wherein X comprises

16. The polynucleotide reagent of claim 11, wherein X comprises

17. The polynucleotide reagent of claim 12, wherein X comprises

* * * * *